(12) United States Patent (10) Patent No.: US 11,026,761 B2
Frushour et al. (45) Date of Patent: Jun. 8, 2021

(54) METHODS OF DETERMINING A RELATIVE STATE OF CHARGE OF A BATTERY FOR A SURGICAL INSTRUMENT AND SURGICAL INSTRUMENTS AND COMPUTER-READABLE MEDIA IMPLEMENTING THE SAME

(71) Applicant: COVIDIEN LP, Mansfield, MA (US)

(72) Inventors: Scott E. M. Frushour, Boulder, CO (US); David J. Van Tol, Boulder, CO (US)

(73) Assignee: Covidien LP, Mansfield, MA (US)

( * ) Notice: Subject to any disclaimer, the term of this patent is extended or adjusted under 35 U.S.C. 154(b) by 485 days.

(21) Appl. No.: 15/888,178

(22) Filed: Feb. 5, 2018

(65) Prior Publication Data

US 2019/0239977 A1 Aug. 8, 2019

(51) Int. Cl.
*H02J 7/00* (2006.01)
*H02J 7/14* (2006.01)
(Continued)

(52) U.S. Cl.
CPC ............ *A61B 90/08* (2016.02); *A61B 17/295* (2013.01); *A61B 17/320092* (2013.01);
(Continued)

(58) Field of Classification Search
USPC ....................................................... 320/132
See application file for complete search history.

(56) References Cited

U.S. PATENT DOCUMENTS 5,137,020 A 8/1992 Wayne et al.
6,064,180 A * 5/2000 Sullivan ................. B60L 58/10
320/132
(Continued)

FOREIGN PATENT DOCUMENTS

EP 3070627 A1 9/2016
EP 3087936 A2 11/2016
WO 2017123841 A2 7/2017

OTHER PUBLICATIONS

Extended European Search Report issued in corresponding European Application No. 19155209.0 dated Jun. 11, 2019, 10 pages.
(Continued)

*Primary Examiner* — Alexis B Pacheco
(74) *Attorney, Agent, or Firm* — Carter, DeLuca & Farrell LLP

(57) ABSTRACT

Methods and surgical instruments are provided for determining a relative state of charge of a battery used during a surgical procedure. The surgical instrument includes an end effector configured to treat tissue with energy, and a user interface configured to receive an input. A generator is coupled to the end effector, and the battery communicates with the generator. A controller includes a processor and a memory having instructions stored thereon which, when executed by the processor, cause the processor to detect an input at the user interface. In response to the detected input at the user interface, a discharge profile is matched to the detected input. The discharge profile corresponds to a discharge curve representing current discharge over time. A relative state of charge is then identified from the discharge curve based on usage of the surgical instrument during a surgical procedure.

7 Claims, 5 Drawing Sheets

(51) Int. Cl.
*A61B 90/00* (2016.01)
*A61B 17/32* (2006.01)
*A61B 34/00* (2016.01)
*A61B 17/295* (2006.01)
*A61B 17/00* (2006.01)

(52) U.S. Cl.
CPC .... *A61B 34/25* (2016.02); *A61B 2017/00221* (2013.01); *A61B 2017/00734* (2013.01); *A61B 2034/258* (2016.02); *A61B 2090/0803* (2016.02); *A61B 2560/028* (2013.01)

(56) References Cited

U.S. PATENT DOCUMENTS

| | | |
|---|---|---|
| 6,490,484 B2 | 12/2002 | Dooley et al. |
| 7,446,510 B2* | 11/2008 | Chou .................. G01R 31/392 320/156 |
| 8,719,195 B2 | 5/2014 | Frisch et al. |
| 8,942,935 B2 | 1/2015 | Michaels et al. |
| 9,310,441 B2 | 4/2016 | Jo |
| 2010/0121588 A1 | 5/2010 | Elder et al. |
| 2010/0191490 A1 | 7/2010 | Martens et al. |
| 2012/0089039 A1* | 4/2012 | Felix ...................... A61B 5/333 600/523 |
| 2013/0323548 A1 | 12/2013 | Iwamoto |
| 2013/0335030 A1* | 12/2013 | Joe ...................... H01M 10/052 320/134 |
| 2015/0084778 A1 | 3/2015 | Mittal et al. |
| 2015/0289925 A1* | 10/2015 | Voegele ............. A61B 18/1233 606/38 |
| 2016/0176309 A1 | 6/2016 | Jeon et al. |
| 2017/0202595 A1 | 7/2017 | Shelton, IV |
| 2017/0333073 A1 | 11/2017 | Faller et al. |
| 2018/0250018 A1* | 9/2018 | Spickermann ...... A61M 1/3653 |
| 2018/0263557 A1* | 9/2018 | Kahlman ................. H02J 50/40 |
| 2019/0386709 A1* | 12/2019 | Woerlee ............... H04B 5/0031 |

OTHER PUBLICATIONS

Communication Pursuant to Article 94(3) EPC issued in corresponding European Application No. 19155209.0 dated Mar. 24, 2021, 5 pages.

* cited by examiner

METHODS OF DETERMINING A RELATIVE STATE OF CHARGE OF A BATTERY FOR A SURGICAL INSTRUMENT AND SURGICAL INSTRUMENTS AND COMPUTER-READABLE MEDIA IMPLEMENTING THE SAME

BACKGROUND

Technical Field

The present disclosure relates to battery-powered surgical instruments, and more particularly, to surgical instrument batteries and methods for determining a relative state of charge for surgical instrument batteries such as ultrasonic surgical instrument batteries.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue. In this regard, an ultrasonic surgical instrument operates by transmitting ultrasonic energy produced by a transducer along a waveguide to an end effector that is spaced-apart from the transducer. With respect to handheld ultrasonic instruments, for example, a portable power source, e.g., a battery, the generator, and the transducer are mounted on the handheld instrument itself, while the waveguide interconnects the generator and transducer with the end effector.

To determine whether a handheld instrument remains sufficiently charged for the endurance of a surgical procedure, a remaining charge of the instrument battery is typically provided to a surgeon during the operation indicating an approximate amount of charge remaining relative to a battery total charge. Though approximations are relatively accurate in systems in which the current discharge is relatively constant, approximating the remaining charge in systems in which current discharge varies becomes more challenging.

SUMMARY

The present disclosure provides a more accurate relative state of charge of the batteries used in handheld surgical instruments such as, for example, handheld ultrasonic surgical instruments. Surgical instruments and methods implementing the teachings of the present disclosure are provided.

According to aspects of the present disclosure, a surgical instrument includes an end effector, a user interface, a generator, a battery, and a controller. The end effector is configured to treat tissue with energy. The user interface is configured to receive an input. The generator is coupled to the end effector, and the battery communicates with the generator. The controller includes a processor, and a memory coupled to the processor. The memory has instructions stored thereon which, when executed by the processor, cause the processor to detect an input at the user interface. In response to the detected input at the user interface, a discharge profile is matched to the detected input. The discharge profile corresponds to a discharge curve representing current discharge over time. A relative state of charge is then identified from the discharge curve based on usage of the surgical instrument during a surgical procedure.

In another aspect of the present disclosure, the memory has further instructions stored thereon which, when executed by the processor, cause the processor to determine whether the identified relative state of charge is below a threshold value, and in response to a determination that the relative state of charge is below the threshold value, providing an indication.

In another aspect of the present disclosure, the received input is a user identifier. In still another aspect of the present disclosure, the received input is a surgical procedure identifier.

According to another aspect of the present disclosure, the memory has further instructions stored thereon which, when executed by the processor, cause the processor to detect a usage of the surgical instrument, and analytically predict a usage pattern based on the detected usage of the surgical instrument. A surgical procedure identifier is then identified based on the predicted usage pattern, and the surgical procedure identifier is matched to the discharge profile.

In another aspect of the present disclosure, the memory has further instructions stored thereon which, when executed by the processor, cause the processor to store data related to use of the surgical instrument during the surgical procedure.

In still another aspect of the present disclosure, the memory has further instructions stored thereon which, when executed by the processor, cause the processor to transmit to a remote storage data related to use of the surgical instrument during the surgical procedure.

According to aspects of the present disclosure, a method is provided for determining a relative state of charge of a battery coupled to a surgical instrument used during a surgical procedure. An input is detected at a user interface of the surgical instrument. In response to the detected input at the user interface, a discharge profile is then matched to the detected input, where the discharge profile corresponds to a discharge curve representing current discharge over time. A relative state of charge is identified from the discharge curve based on usage of the surgical instrument during the surgical procedure.

In another aspect, the method may also include determining whether the identified relative state of charge is below a threshold value, and in response to a determination that the relative state of charge is below the threshold value, providing an indication.

In another aspect of the present disclosure, the method includes collecting historical data related to energy usage from a plurality of ultrasonic surgical instruments. The collected historical data is analyzed to identify different discharge profiles, and each discharge profile is associated with a corresponding surgical procedure.

According to an aspect, a surgical procedure identifier is assigned to each discharge profile, and the detected input includes one of the surgical procedure identifiers. According to another aspect, each discharge profile is associated with a corresponding user.

In another aspect of the present disclosure, the associating includes assigning a user identifier to each discharge profile, and the detected input includes one of the user identifiers.

In still another aspect of the present disclosure, the method further includes detecting a usage of the surgical instrument, and analytically predicting a usage pattern based on the detected usage of the surgical instrument. A surgical procedure identifier is identified based on the predicted usage pattern, and the surgical procedure identifier is matched to the discharge profile.

In another aspect of the present disclosure, data related to use of the surgical instrument during the surgical procedure is stored.

According to another aspect of the present disclosure, data related to use of the surgical instrument is transmitted to a remote storage during the surgical procedure.

In aspects of the present disclosure, a non-transitory computer-readable medium is provided having instruction stored thereon, which when executed by a processor, cause the processor to perform a method of estimating a relative state of charge of a battery coupled to a surgical instrument used during a surgical procedure. The method includes the steps of detecting an input at a user interface of the surgical instrument, and in response to the detected input at the user interface, matching a discharge profile to the detected input, the discharge profile corresponding to a discharge curve representing current discharge over time. A relative state of charge is identified from the discharge curve based on usage of the surgical instrument during the surgical procedure.

In another aspect of the present disclosure, the method further comprises determining whether the identified relative state of charge is below a threshold value, and in response to a determination that the relative state of charge is below the threshold value, providing an indication.

In still another aspect of the present disclosure, historical data related to energy usage is collected from a plurality of ultrasonic surgical instruments, and the collected historical data is analyzed to identify different discharge profile. Each discharge profile is then associated with a surgical procedure.

In still another aspect of the present disclosure, a usage of the surgical instrument is detected, and a usage pattern is analytically predicted based on the detected usage of the surgical instrument. A surgical procedure identifier is identified based on the predicted usage pattern, and the surgical procedure identifier is matched to the discharge profile.

BRIEF DESCRIPTION OF THE DRAWINGS

Various aspects and features of the present disclosure are described herein with reference to the drawings wherein.

DETAILED DESCRIPTION

Figure 5B:
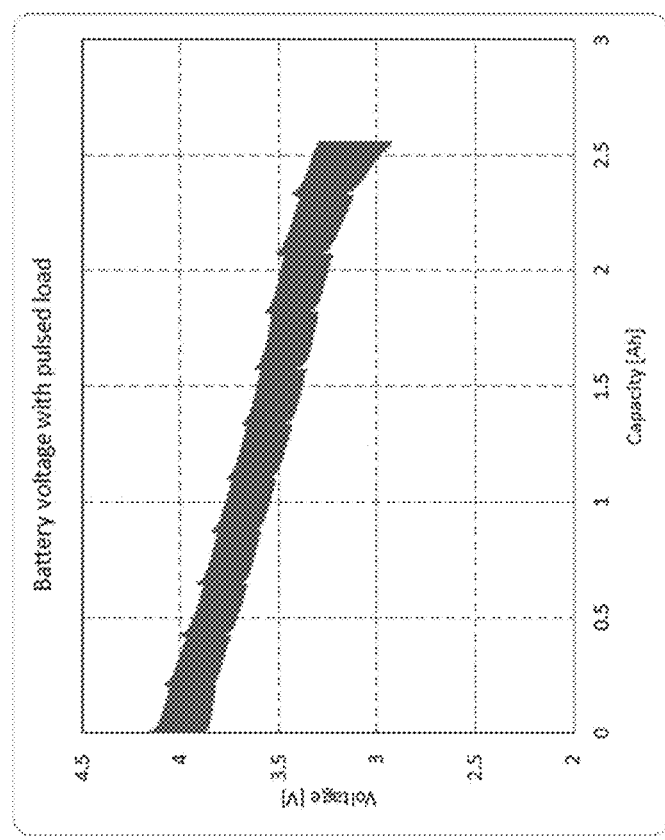
FIGS. 5A and 5B are exemplary battery discharge curves for a constant load and pulsed load, respectively.
Figure 5A:
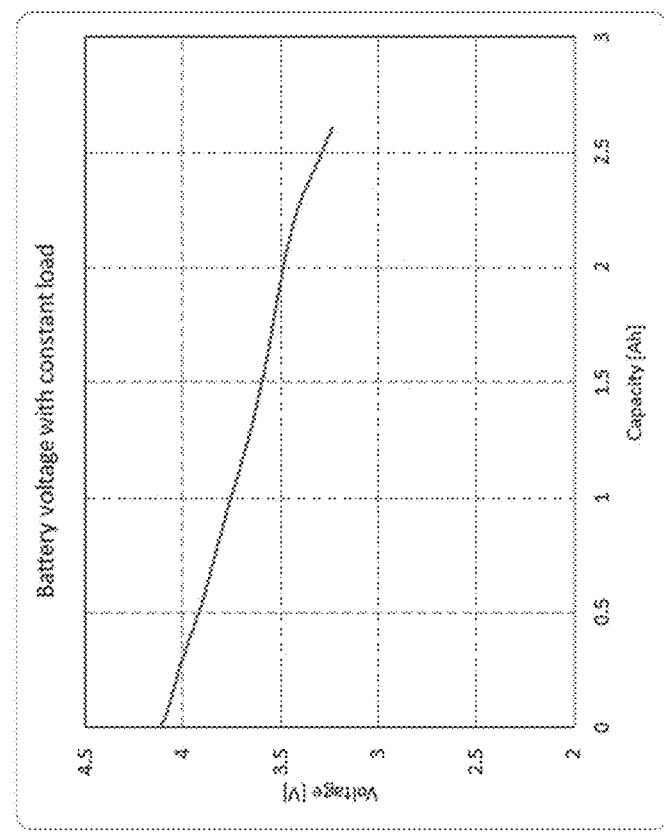

The present disclosure provides methods and surgical instruments implementing methods for estimating a relative state of charge of a battery, where the battery is implemented into a variable current discharge instrument, such as an ultrasonic surgical instrument. In this regard, historical data related to the current discharge of one or more instruments is collected and analyzed for usage patterns over time. Once identified, the usage patterns are assigned a surgical procedure identifier and/or a user identifier and stored with the identifier along with a corresponding discharge output curve (exemplary discharge output curves are illustrated in FIGS. 5A and 5B for a constant load and pulsed load, respectively). When an instrument is used for a present surgical procedure, the user may either input a unique user identifier and/or a surgical procedure identifier, and the inputted identifier is matched to its corresponding discharge output curve to provide a more accurate reflection of the current being discharged during the present surgical procedure. In another embodiment, predictive analytics may be applied to the usage of the surgical instrument to identify a usage pattern, which is then matched to a corresponding discharge output curve. In these ways, a battery may be less susceptible to being overcharged, and battery life may be extended.

For the purposes herein, the present disclosure is described in the context of ultrasonic surgical instrument 10, which is generally described. As the methods for estimating relative state of charge may be implemented in any one of numerous surgical instruments that operate by variably discharging current, aspects and features of ultrasonic surgical instrument 10 not germane to the understanding of the estimation of the relative state of charge features provided in accordance with the present disclosure are omitted to avoid obscuring such aspects and features of the present disclosure in unnecessary detail.

Figure 1:
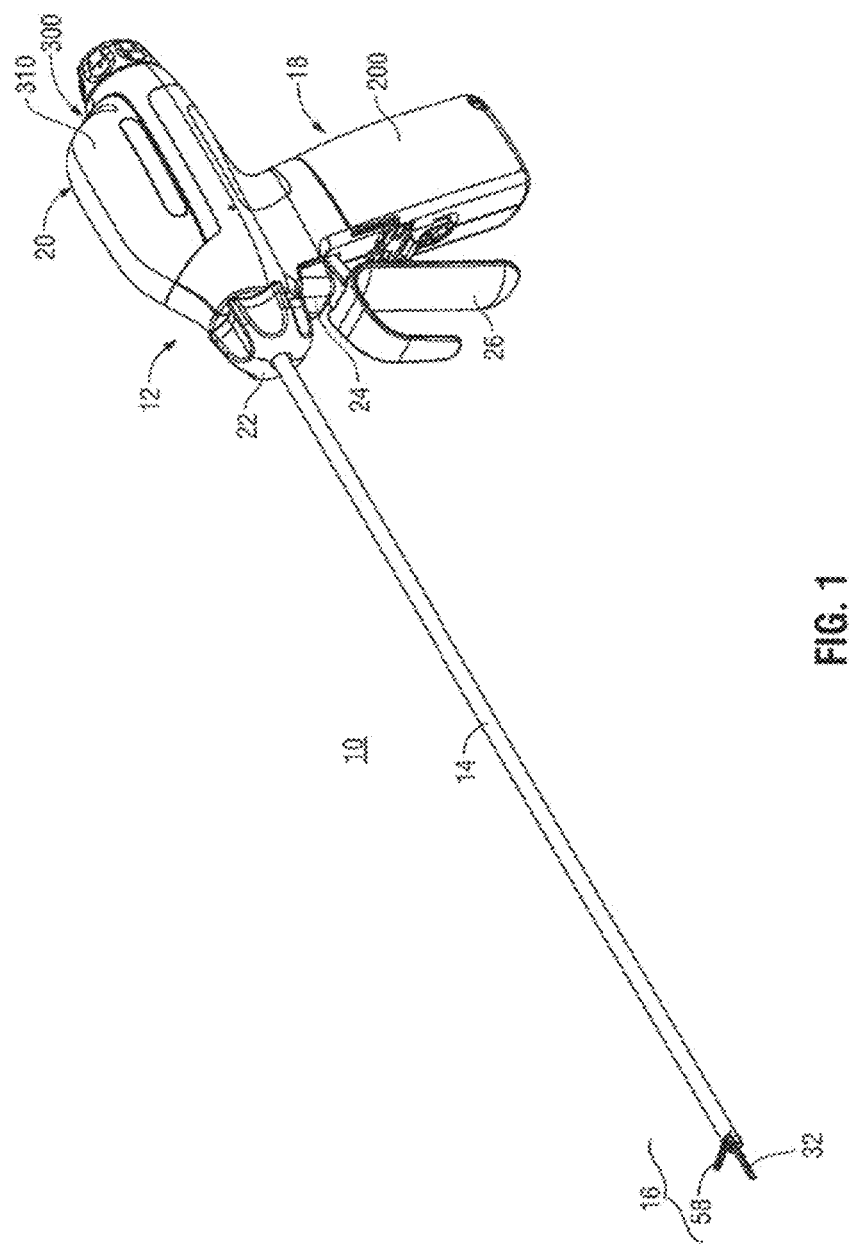
FIG. 1 is a perspective view of an ultrasonic surgical instrument, according to an embodiment.

With reference to FIG. 1, ultrasonic surgical instrument 10 includes a handle assembly 12, an elongated body portion 14, and a tool assembly 16. Tool assembly 16 includes an end effector configured to ultrasonically dissect and/or coagulate tissue. In this regard, tool assembly 16 includes a blade 32 and a clamp member 58. Handle assembly 12 supports a battery assembly 18 and an ultrasonic transducer and generator assembly ("TAG") 20, and includes a rotatable nozzle 22, an activation button 24, and a clamp trigger 26. Battery assembly 18 and TAG 20 are each releasably secured to handle assembly 12, and are removable therefrom to facilitate disposal of the entire device, with the exception of battery assembly 18 and TAG 20. However, it is contemplated that any or all of the components of ultrasonic surgical instrument 10 be configured as disposable single-use components or sterilizable multi-use components.

Elongated body portion 14, tool assembly 16, rotatable nozzle 22, activation button 24, and clamp trigger 26 make up a disposable portion of ultrasonic surgical instrument 10. Elongated body portion 14 includes a waveguide (not shown) extending therethrough distally from handle assembly 12 to tool assembly 16. A distal end of the waveguide defines blade 32. A proximal end of the waveguide is configured to engage TAG 20. Clamp member 58 is moved between the open and closed positions in response to actuation of clamp trigger 26. Specifically, when clamp trigger 26 is compressed towards battery assembly 18, an outer actuator tube of elongated body portion 14 is moved from the advanced position to the retracted position to pivot clamp member 58 from the open position to the closed position in relation to blade 32. A spring (not explicitly shown) may be provided to bias clamping trigger 26 towards the initial position and, thus, clamp member 58 towards the open position.

Activation button 24 is supported on handle assembly 12. When activation button 24 is activated in an appropriate manner, an underlying two-mode switch assembly 170 (FIG. 2) is activated to effect communication between battery assembly 18 and TAG 20 to drive TAG 20 in either a "LOW" power mode or a "HIGH" power mode, depending upon the manner of activation of activation button 24.

Figure 2:
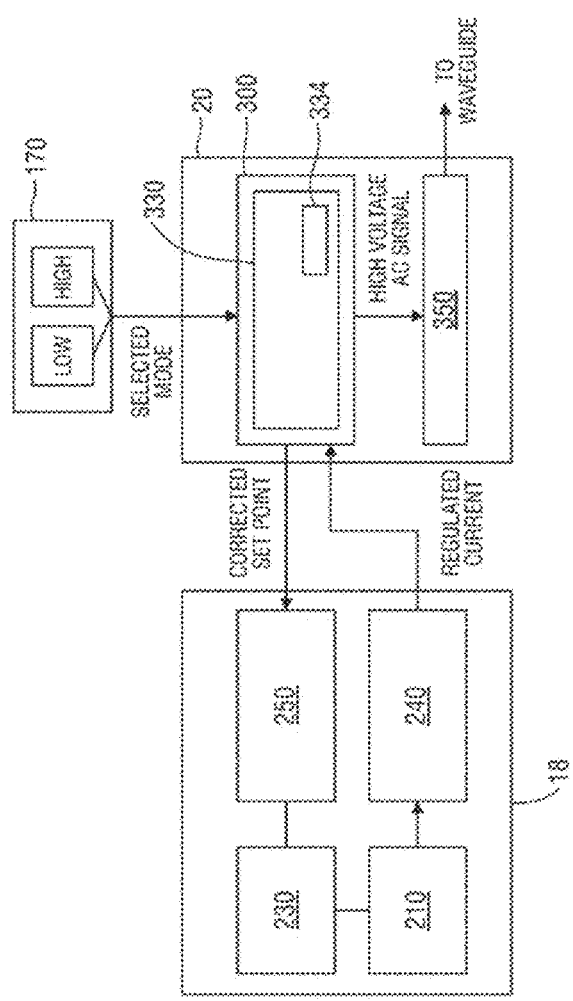
FIG. 2 is a simplified block diagram of a battery and an ultrasonic transducer and generator assembly implemented in the ultrasonic surgical instrument of FIG. 1, according to an embodiment.

Battery assembly 18 is connected to a lower end of handle assembly 12 to define a fixed handgrip portion of handle assembly 12 and is disposed in an outer housing 200. With reference to FIG. 2, battery assembly 18 houses one or more battery cells 210, a safety circuit and fuel gauge board 230, a buck converter 240, and a battery microcontroller 250.

According to an embodiment, buck converter 240 is a DC-to-DC converter, which receives unregulated DC voltage from one of the battery cells 210 and supplies a regulated and reduced DC output voltage to TAG 20. A series of contacts (not explicitly shown) enable communication of power and/or control signals between the internal components of battery assembly 18, two-mode switch assembly 170, and TAG 20, although contactless communication therebetween is also contemplated.

Safety circuit and fuel gauge board 230 of battery assembly 18 controls the charging and discharging of battery cells 210, monitors parameters of battery cells 210, and protects battery cells 210. In this regard, safety circuit and fuel gauge board 230 monitors battery cells 210 to estimate remaining capacity and full charge capacity of battery cells 210 and also calculates the relative state of charge (RSOC) of battery cells 210. The RSOC is the remaining capacity as a percentage of the full charge capacity.

Figure 3:
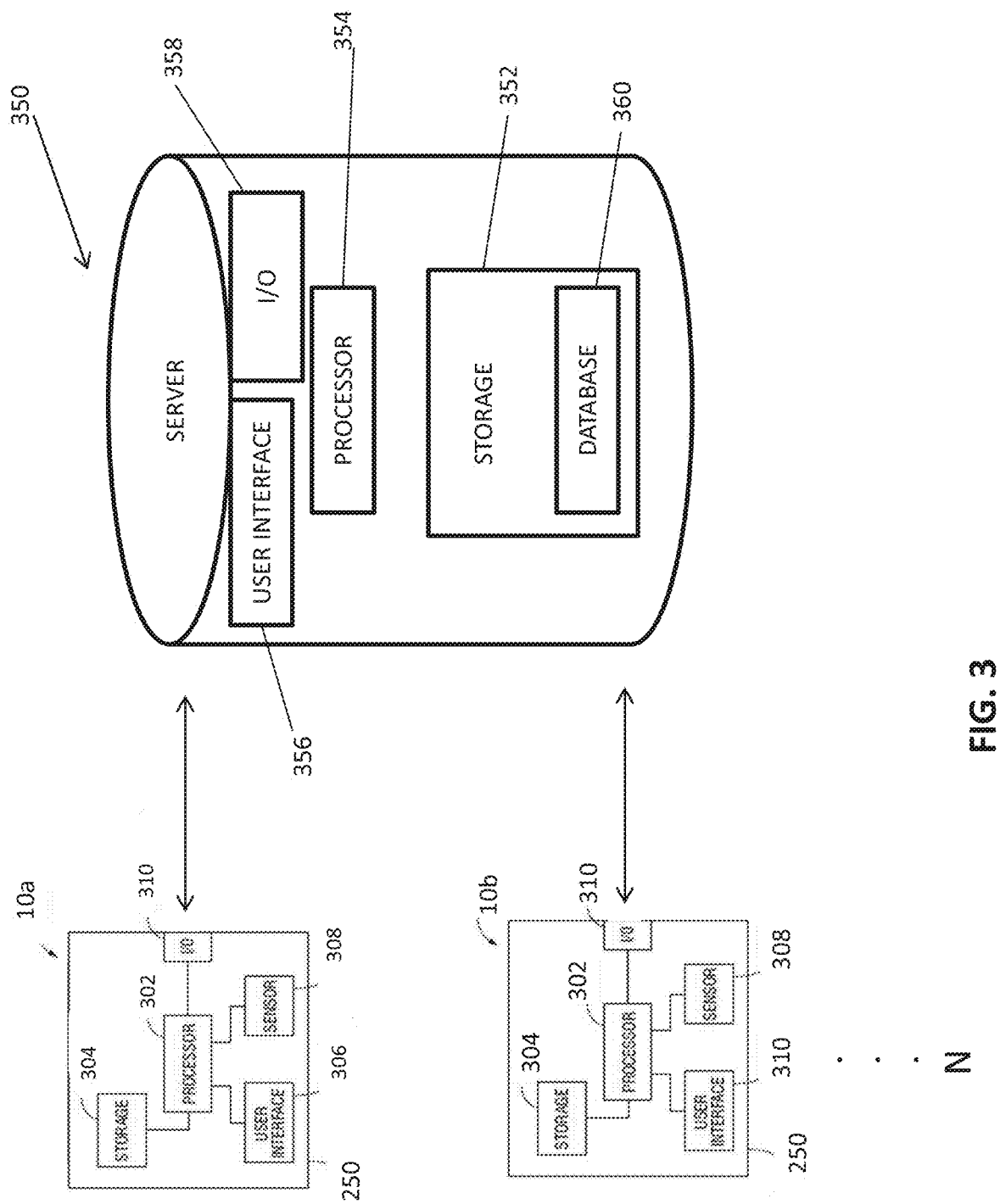
FIG. 3 is a simplified block diagram of a system architecture of a plurality of ultrasonic surgical instruments and a server, according to an embodiment.

In addition to controlling buck converter 240, battery microcontroller 250 is configured to receive a user input, generate an audio signal to drive a speaker coupled to battery assembly 18, monitor the state of activation button 24 and safety circuit and fuel gauge board 230, and communicate the states to TAG 20. As shown in a simplified block diagram of a system including one or more ultrasonic surgical instruments 10a, 10b, . . . N (collectively referenced as ultrasonic surgical instrument 10) in FIG. 3, each instrument 10 has a battery microcontroller 250, which includes a processor 302, a storage device 304, and communicates with a user interface 306, a sensor 308, and an input/output 310.

Processor 302 may include any suitable component(s), e.g., a central processing unit (CPU) and a memory, operable to execute instructions to operate the one or more surgical instruments 10 and to receive, process, manipulate, and/or output the information stored in storage device 304. Storage device 304 is coupled to processor 302 and may include any suitable component(s), e.g., a magnetic disk, flash memory, optical disk, or other suitable data storage device, operable for storing surgical instrument information obtained during the use of the one or more surgical instruments 10 and/or instructions, which when executed by processor 302, cause processor 302 determine the RSOC of battery cells 210.

User interface (UI) 306 communicates with processor 302 and includes any actuators, buttons, switches, GUI's, etc. of ultrasonic surgical instrument 10 such as activation button 24. Inputs into UI 306 may directly operate the one or more surgical instruments 10, e.g., in the case of mechanical component, electromechanical components, or electrical switching components. Alternatively or additionally, inputs into UI 306 may be fed to processor 302 to enable processor 302 to operate ultrasonic surgical instrument 10 in accordance with the input(s) provided and/or communicate with other devices, such as server 350, to effect operation of ultrasonic surgical instrument 10 in a particular manner. Some or all of the information utilized in operating ultrasonic surgical instrument 10, as can be appreciated, is stored in storage device 304 as surgical instrument information. UI 306 may also allow for the input of data, instructions, settings, etc., which may also constitute surgical instrument information to be stored in storage device 302.

Sensors 308 may include distinct sensor components disposed on or separate from ultrasonic surgical instrument 10 and/or may be incorporated into components thereof, e.g., processor 302 and/or UI 306, in electrical, mechanical, electromechanical, software, hardware, combinations thereof, or other suitable configurations so as to enable the collection of surgical instrument information during use of ultrasonic surgical instrument 10. Thus, sensors 308 are capable of sensing a number, pattern, sequence, and/or density of ultrasonic activations, power level settings, e.g., high power or lower power, corresponding to each ultrasonic activation, time durations of ultrasonic activations, electrical parameters of the generator, transducer, and/or battery of ultrasonic surgical instrument 10, temperature or other feedback data received from ultrasonic surgical instrument 10 regarding ultrasonic surgical instrument 10 and/or patient tissue, etc.

The information obtained by sensors 308 is stored in storage device 304 as surgical instrument information. Input/output 310 is provided to facilitate communication of the surgical instrument information from storage device 304 to other devices such as server 350. Input/output 310 may be configured for wired or wireless communication and may communicate the surgical instrument information in real-time, periodically, upon occurrence of a particular even (entry into standby mode, connection to a charger or other device, etc.), and/or upon request. Input/output 310 also enables the input of software updates.

In addition or as an alternative to storing surgical instrument information in storage device 304, battery microcontroller 250 may communicate the surgical instrument information to a server 350. Server 350 may include, for example, one or more storage devices 352, a processor 354, a UI 356, and an input/output 358. Storage devices 352 may include any suitable component(s), e.g., a magnetic disk, flash memory, optical disk, or other suitable data storage device, operable for storing surgical instrument information and/or procedure information and may additionally or alternatively store information that may be transmitted or accessed to facilitate processing of the surgical instrument information and/or procedure information. For example, storage devices 352 may store data from surgical instrument manufacturers regarding the surgical instrument(s) 10 to enable the interpretation of the surgical instrument information, may serve as an electronic medical record repository from which procedure information may be retrieved, and the like.

Processor 354 may include any suitable component(s), e.g., a central processing unit (CPU) and a memory, operable to execute instructions to receive, process, manipulate, store, and/or output information. For example, processor 354 executes instructions to process, manipulate, and store the surgical instrument information and procedure information for each surgical procedure and to store the same in one or more searchable databases to enable the use of such information. User interface (UI) 356 includes any GUI, keyboard, mouse, etc. that enable, for example, the input of patient information and/or procedure information. Input/output 358 is configured to enable the receipt and/or transmission of surgical instrument information, procedure information, and/or other information useful in processing the surgical instrument information and/or procedure information. Some or all of this information may be processed, manipulated, and stored in storage devices 352, e.g., in one or more searchable databases 360. In an embodiment, processor 354 may be configured to search such database(s) of storage devices 352 and identify similarities and/or correlations between a surgical procedure that will be performed or has been performed (referred to hereinbelow as a "present surgical procedure") and that of historical cases stored in the database(s).

Although described as communicating with one ultrasonic surgical instrument 10a, server 350 may be in communication with multiple ultrasonic surgical instruments (e.g., ultrasonic surgical instrument 10b ... 10N) in order to receive and/or transmit surgical instrument information, procedure information, and/or other information useful in processing the surgical instrument information and/or procedure information.

Due to a variety of factors, current discharge can vary from very low to extremely high when using ultrasonic surgical instrument 10 during a surgical procedure. For example, due to the two mode operability of ultrasonic surgical instrument 10, when the instrument primarily is used in a high mode, doing so will discharge battery cell 210 faster than when the instrument is used in a low mode, and vice versa. In another example, during a surgical procedure using both cold steel instruments (or other instrumentation) and ultrasonic surgical instrument 10, the cold steel instruments (or other instrumentation) may be used more often than ultrasonic surgical instrument 10, which may place ultrasonic surgical instrument 10 in a quiescent state for a long period of time. As a result, battery cell 210 may discharge much slower than in instances in which ultrasonic surgical instrument 10 is used more often. In addition, the low and high current discharges can each be delivered in short bursts or for prolonged periods of time. As such, rather than estimating RSOC based on standard discharge profiles and couloumb counting, current usage energy patterns are matched with stored discharge profiles, which provide corresponding RSOC discharge curves, where the potential of battery cell 210 is plotted with respect to its full charge capacity over time, to more closely reflect actual discharge of the battery.

Figure 4:
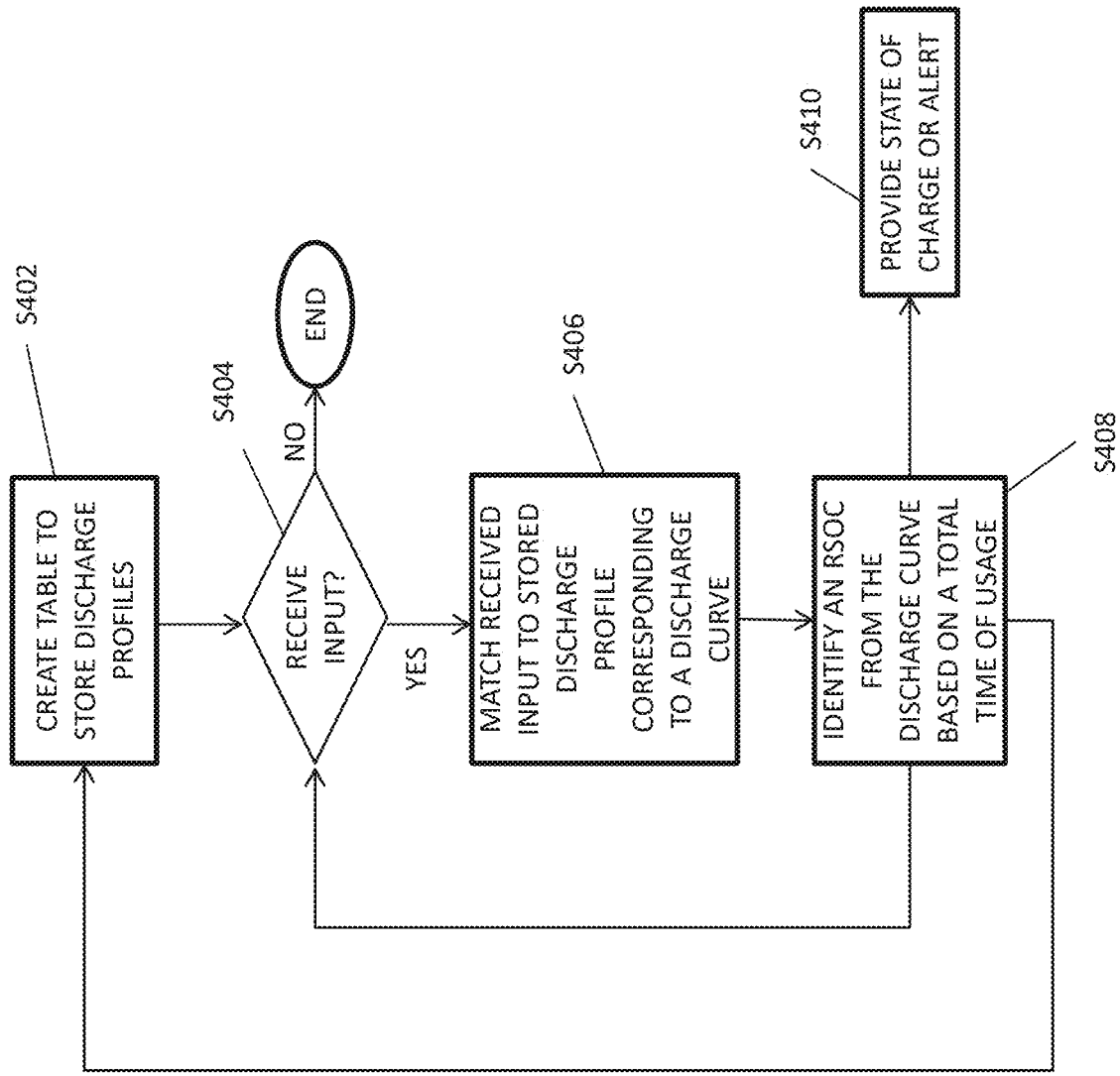
FIG. 4 is a flow diagram of a method of estimating a relative state of charge of a variable current discharge instrument, according to an embodiment.

In this regard as illustrated in FIG. 4, a method 400 is provided for determining a RSOC of a variable discharge surgical instrument, such as ultrasonic surgical instrument 10. According to an embodiment, a table is created storing discharge profiles at step S402. Specifically, data related to energy usage is collected from one or more surgical instruments, such as ultrasonic surgical instruments 10a ... N, and stored. For example, surgical instrument information, procedure information, a number, pattern, sequence, and/or density of ultrasonic activations, power level settings, e.g., high power or lower power, corresponding to each ultrasonic activation, time durations of ultrasonic activations, electrical parameters of the generator, transducer, and/or battery of ultrasonic surgical instrument 10, temperature or other sensed or feedback data are collected.

It will be appreciated that when ultrasonic surgical instrument 10 is used for different surgical procedures and/or by different users, the different energy usages generate different discharge curves. According to an exemplary embodiment, the number, pattern, sequence, duration, power level, and/or density of activations used during a laparoscopic colectomy procedure are not the same as those used in the performance of a gastrectomy procedure or another surgical procedure. As such, each different surgical procedure may be identifiable by a unique discharge curve. Further still, for each particular surgical procedure, each user may have a different preference of power level, duration, and hence, a unique discharge curve that is output during the operation of ultrasonic surgical instrument 10.

The data related to the energy usage of ultrasonic surgical instruments may be collected from a plurality of different users in a variety of manners. For example, a user may choose to upload the energy usage data to a database, such as database 360, ultrasonic surgical instrument 10 may include instructions to automatically store the energy usage data in storage device 304 or transmit the energy usage data to storage device 352 of server 350, and/or a field service engineer may tag certain energy usage data to be uploaded to storage device 352 of server 350.

The stored data is analyzed to identify different usage patterns, which are used to create discharge profiles, such as the exemplary battery discharge curves for a constant load and pulsed load illustrated in FIGS. 5A and 5B, respectively. For example, the variables related to each use of ultrasonic surgical instrument 10 during a particular procedure, such as the number, pattern, sequence, duration, power level, and/or density of activations, or other data related to energy usage, are analyzed for specific patterns as a function of time. As alluded to above, due to their uniqueness, each usage pattern corresponds to a unique discharge curve, which plots the RSOC as a function of time. Usage patterns are grouped together and each group is categorized into different types of surgical procedures and/or different users. Discharge profiles are created by associating each type of surgical procedure with a particular identifier (for example, a surgical procedure identifier) and each user with a particular identifier (for example, a user identifier). The surgical procedure identifier and the user identifier each may be a string of unique combinations of characters, symbols, letters, numbers, or other identifying marks. Each discharge profile further corresponds to a unique discharge curve, which can be used to interpolate energy usage by a user that will use the surgical instrument for a particular surgical procedure. In any case, the discharge profiles are stored as look-up tables or in other formats either in storage device 304 to be retrieved locally or in storage device 352 of server 350 to be retrieved remotely.

By creating discharge profiles in the manner described above, the RSOC of battery cells 210 may be more accurately determined. In an embodiment of the present disclosure, an input related to an anticipated use and/or an anticipated user of the surgical instrument is received at step S404. According to an embodiment of the present disclosure, a surgical procedure may be selected as the present surgical procedure intended to be performed and/or a user to use the surgical instrument in the present surgical procedure may be selected as part of procedure planning. For example, a selection may be detected at a user interface at a mobile device, smartphone, or computer, or another device capable of communicating with processor(s) 302, 352. Alternatively, a user identifier and/or a surgical procedure identifier may be entered. In still another embodiment, the user may simply commence performance of the present surgical procedure, and predictive analytics are applied to predict a usage pattern based on the commenced usage in order to identify the present surgical procedure and associate a surgical procedure identifier therewith. In any case, the lookup table is used to match the received input (for example, the user and/or surgical procedure identifier) to a corresponding stored discharge profile at step S406.

As noted above, each discharge profile is associated with a discharge curve (see, e.g., the exemplary discharge curves in FIGS. 5A and 5B). Thus, the discharge curve for the discharge profile matched from step S406 is used to calculate discharge of batteries 210 for the present surgical procedure. In an embodiment in which the user and/or surgical procedure identifier are used, the corresponding discharge profile and its associated discharge curve are retrieved from storage. According to an embodiment, usage data related to the surgical instrument for the present surgical procedure is either concurrently transmitted to or is stored in storage device 352 of server 350 or in storage device 304 to be used as historical data to further train the discharge profiles. In another embodiment, usage data related to the surgical instrument for the present surgical procedure is flagged so that when a service technician retrieves the usage data, the flagged data is transmitted to a central repository, such as server 350 or other central storage.

To determine the RSOC using the discharge curve, the total time of the surgical instrument usage during the present surgical procedure is matched with an RSOC value corresponding to the total time at step S408. The total time of the surgical instrument usage is the total (cumulative) activated time of the surgical instrument during a surgical procedure. The RSOC value may be provided as a relative state of charge, for example as a visual output, or may be compared with a threshold value and output as an audible or visual alert at step S410. In an embodiment, to determine whether ultrasonic surgical instrument 10 has a sufficient amount of remaining charge, the RSOC may be compared to a threshold value and, if below a threshold value, an alert may be tactilely, audibly and/or visually output, for example, to the user of instrument 10, to indicate that ultrasonic surgical instrument 10 should be recharged. Alternatively or additionally, the remaining state of charge may be displayed, for example, as a percentage of a full charge, to indicate battery life.

Method 400 then iterates at step S404. In the event that ultrasonic surgical instrument 10 is not recharged after use, the most recent RSOC is used as a starting RSOC to be updated.

In embodiments, depending upon user input and/or usage of the surgical instrument, the matched discharge profile may change to a different discharge profile. This may be the result of a change in the user and/or surgical procedure identifier during a procedure, a change in the anticipated use and/or an anticipated user input during the procedure, and/or a change in the result of the predicted usage pattern. As such, should circumstances change during a surgical procedure, the matched discharge profile may be dynamically changed to a different discharge profile that better represents the changed circumstances.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    an end effector configured to treat tissue with ultrasonic energy;
    a user interface for receiving an input;
    a generator coupled to the end effector;
    a battery in communication with the generator; and
    a controller coupled to the battery, the controller including:
        a processor; and
        a memory coupled to the processor, the memory storing a plurality of discharge profiles and having instructions stored thereon which, when executed by the processor, cause the processor to:
            detect an input at the user interface,
            in response to the detected input at the user interface, match a discharge profile among the plurality of discharge profiles to the detected input, the discharge profile corresponding to a discharge curve representing current discharge over time,
            identify a relative state of charge from the discharge curve based on usage of the surgical instrument during a surgical procedure, and
            provide the identified relative state of charge as an output.

2. The surgical instrument of claim 1, wherein the memory has instructions stored thereon which, when executed by the processor, further cause the processor to determine whether the identified relative state of charge is below a threshold value, and in response to a determination that the relative state of charge is below the threshold value, provide the output.

3. The surgical instrument of claim 1, wherein the received input is a user identifier.

4. The surgical instrument of claim 1, wherein the received input is a surgical procedure identifier.

5. The surgical instrument of claim 1, wherein the memory has instructions stored thereon which, when executed by the processor, further cause the processor to:
    detect a usage of the surgical instrument,
    analytically predict a usage pattern based on the detected usage of the surgical instrument,
    identify an identifier based on the predicted usage pattern, and
    match the identifier to the discharge profile.

6. The surgical instrument of claim 1, wherein the memory has instructions stored thereon which, when executed by the processor, further cause the processor to:
    store data related to usage of the surgical instrument during the surgical procedure.

7. The surgical instrument of claim 1, wherein the memory has instructions stored thereon which, when executed by the processor, further cause the processor to:
    transmit to a remote storage data related to usage of the surgical instrument during the surgical procedure.

* * * * *